US012721963B2

(12) United States Patent
Mills et al.

(10) Patent No.: US 12,721,963 B2
(45) Date of Patent: *Sep. 1, 2026

(54) SYSTEM AND METHOD FOR TRACKING ANESTHETIC AGENT IN A VAPORIZER RESERVIOR

(71) Applicant: General Electric Company

(72) Inventors: Julie Anne Mills, Monona, WI (US); Joseph Lacey, Madison, WI (US); Thomas Bender, II, Cottage Grove, WI (US); Russell Kuzelka, McFarland, WI (US); David Michael Wahl, Verona, WI (US)

(73) Assignee: GE Precision Healthcare LLC, Waukesha, WI (US)

(*) Notice: Subject to any disclaimer, the term of this patent is extended or adjusted under 35 U.S.C. 154(b) by 1314 days.

This patent is subject to a terminal disclaimer.

(21) Appl. No.: 17/491,021

(22) Filed: Sep. 30, 2021

(65) Prior Publication Data

US 2022/0016385 A1 Jan. 20, 2022

Related U.S. Application Data

(63) Continuation of application No. 15/987,720, filed on May 23, 2018, now Pat. No. 11,154,686.

(51) Int. Cl.

| | |
|---|---|
| *A61M 16/18* | (2006.01) |
| *A61M 16/00* | (2006.01) |
| *A61M 16/10* | (2006.01) |
| *G01F 1/667* | (2022.01) |
| *G01F 1/74* | (2006.01) |

(52) U.S. Cl.

CPC .......... *A61M 16/18* (2013.01); *A61M 16/104* (2013.01); *G01F 1/667* (2013.01); (Continued)

(58) Field of Classification Search

CPC ................ A61M 16/18; A61M 16/104; A61M 2016/0027; A61M 2016/003; A61M 2016/1035; A61M 2205/18; A61M 2205/3334; A61M 2205/3375; A61M 16/0051; A61M 16/085; A61M 16/208; A61M 16/22; A61M 2205/17; A61M 2205/3306; A61M 2205/3327; A61M 16/01; A61M 16/024; A61M 16/0891; A61M 2016/0033; A61M 2205/3331; A61M 2205/3368; A61M 2205/3389; (Continued)

(56) References Cited

U.S. PATENT DOCUMENTS 7,565,905 B2 * 7/2009 Hickle .................. A61M 16/01 128/203.14

9,592,357 B2 * 3/2017 Heinonen .............. G16H 20/40

(Continued)

*Primary Examiner* — Kendra D Carter
*Assistant Examiner* — Maap Ellabib

(57) ABSTRACT

A system for tracking anesthetic agent in a vaporizer reservoir can include a mass flow sensor configured to measure a flow rate entering or exiting a vaporizer chamber, a gas pressure sensor configured to measure a pressure of a mixed gas provided from the vaporizer chamber, and a processor to calculate a remaining agent time based on at least the gas flow rate, the pressure of the mixed gas, and an anesthetic concentration in the mixed gas. The processor can also provide the remaining agent time for display to a clinician.

17 Claims, 7 Drawing Sheets

(52) U.S. Cl.
CPC ....... *G01F 1/74* (2013.01); *A61M 2016/0027* (2013.01); *A61M 2016/003* (2013.01); *A61M 2016/1035* (2013.01); *A61M 2205/18* (2013.01); *A61M 2205/3334* (2013.01); *A61M 2205/3375* (2013.01)

(58) Field of Classification Search
CPC .... A61M 2205/3653; A61M 2205/502; A61M 2205/581; A61M 2205/583; A61M 16/18183; G01F 1/667; G01F 1/74
See application file for complete search history.

(56) References Cited

U.S. PATENT DOCUMENTS

| | | | | |
|---|---|---|---|---|
| 2002/0069876 | A1* | 6/2002 | Loser | A61M 16/18 128/203.19 |
| 2010/0269820 | A1* | 10/2010 | Danielsen | A61M 16/0051 128/203.14 |
| 2011/0056491 | A1* | 3/2011 | Rumph | A61M 16/209 128/203.14 |
| 2012/0240928 | A1* | 9/2012 | Bottom | G01F 1/66 128/203.14 |
| 2013/0276782 | A1* | 10/2013 | Larsson | A61M 16/18 128/203.14 |
| 2014/0352693 | A1* | 12/2014 | Pessala | A61M 16/0051 128/203.14 |
| 2015/0320953 | A1* | 11/2015 | Acker | A61M 16/204 128/203.14 |
| 2016/0008567 | A1* | 1/2016 | Bottom | A61M 16/20 128/200.23 |
| 2017/0128677 | A1* | 5/2017 | Eilat | B05B 7/2421 |
| 2018/0093063 | A1* | 4/2018 | Rajan | A61M 16/0066 |

* cited by examiner

50
Gas concentration sensor
14
18
26
27
28
25
48
49
37
36
44
Vaporizer chamber
P
39
41
Injector
35
Reservoir
Accum.
38
Pump
33
31
29
43
Gas mass flow sensor
Gas regulating unit
13

SYSTEM AND METHOD FOR TRACKING ANESTHETIC AGENT IN A VAPORIZER RESERVIOR

CROSS-REFERENCE TO RELATED APPLICATIONS

The present application is a continuation of and claims priority to U.S. patent application Ser. No. 15/987,720, filed on May 23, 2018 and titled "SYSTEM AND METHOD FOR TRACKING ANESTHETIC AGENT IN A VAPORIZER RESERVOIR," which is incorporated herein by reference in its entirety.

BACKGROUND

The present disclosure generally relates to systems and methods of monitoring the amount of anesthetic agent in a vaporizer reservoir, and more specifically to methods and systems of monitoring and reporting anesthetic agent fill level based on the amount of anesthesia delivery time provided by the available agent in the vaporizer reservoir.

An anesthesia system may be implemented to deliver a predetermined dosage of anesthetic agent to a patient. The anesthesia system may be pneumatically connected to a vaporizer. Conventional vaporizers comprise a sump adapted to retain a liquid anesthetic agent, and a vaporization chamber adapted to convert the liquid anesthetic agent into a gas. The gaseous anesthetic agent is inhaled into the patient's lungs to produce an effect such as pain management, unconsciousness, preventing memory formation, and/or paralysis.

An anesthesiologist or other clinician monitors the level of anesthetic agent in the vaporizer to ensure sufficient anesthetic agent is available for treatment of a patient. In presently available systems, the level of the anesthetic agent may be viewed through a glass tube or transparent portion of the vaporizer, referred to as a sight glass. As the anesthetic agent is vaporized, the liquid level of the anesthetic goes down and the agent can be seen visually to fall in the sight glass, providing a visual approximation of the level of anesthetic agent remaining in the vaporizer.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a system for tracking anesthetic agent in a vaporizer reservoir includes a mass flow sensor configured to measure a gas flow rate entering or exiting a vaporizer chamber, a gas pressure sensor configured to measure a pressure of a mixed gas provided from the vaporizer chamber, a gas temperature sensor configured to measure a temperature of the mixed gas provided from the vaporizer chamber, and an agent time module executable on a processor. The agent time module is configured to calculate a remaining agent time based on at least the gas flow rate, the pressure of the mixed gas, the temperature of the mixed gas, and an anesthetic concentration in the mixed gas. The remaining agent time is then provided for display on a display device.

In one embodiment, a system for tracking anesthetic agent in a vaporizer reservoir includes an injector pressure sensor configured to sense a pressure of the anesthetic agent provided to an injector delivering liquid anesthetic agent to the vaporizer reservoir, an injector temperature sensor configured to sense a temperature of the anesthetic agent provided to the injector, and an agent time module executable on the processor to receive a current agent amount and calculate a remaining agent time based on the pressure of the anesthetic agent, the temperature of the anesthetic agent, an orifice size of the injector, at least one of an injection frequency and injection duration of the injector and the current agent amount. The remaining agent time is then provided for display to a clinician.

A method for tracking anesthetic agent in a vaporizer reservoir within an anesthesia vaporizer system includes measuring a gas flow rate entering or exiting a vaporizer chamber, measuring a pressure of a mixed gas provided from the vaporizer chamber, measuring a temperature of the mixed gas provided from the vaporizer chamber, identifying an anesthetic concentration in the mixed gas provided from the vaporizer chamber, and identifying an agent amount of anesthetic agent in the vaporizer reservoir. A dispense rate is then calculated based on the anesthetic concentration, the gas flow rate, the pressure of the mixed gas, and the temperature of the mixed gas. A remaining agent time is then calculated based on at least the agent amount and the dispense rate, and the remaining agent time is provided for display to a clinician. A method for directing anesthetic agent in a vaporizer reservoir includes measuring a pressure of the anesthetic agent provided to an injector delivering anesthetic agent to the vaporizer reservoir, measuring a temperature of the anesthetic agent provided to the injector, and identifying a current agent amount of anesthetic agent in the vaporizer reservoir. A dispense rate is then calculated based on the pressure of the anesthetic agent, the temperature of the anesthetic agent, and orifice size of the injector and at least one of an injection frequency and an injection duration of the injector. A remaining agent time is then calculated based on at least the agent amount and the dispense rate.

An anesthetic agent tracking system for tracking anesthetic agent in a vaporizer reservoir within an anesthesia vaporizer system includes an agent level sensor that measures an agent level of anesthetic agent in the vaporizer reservoir and an agent time module executable on a processor. The agent time module is configured to receive agent level measurements from the agent level sensor over time and to calculate a dispense rate based upon the agent level measurements. A remaining agent time is calculated based on a current agent level measurement and the dispense rate, and the remaining agent time is provided for display to a clinician.

A method for tracking anesthetic agent in a vaporizer reservoir includes measuring an agent level of anesthetic agent in the vaporizer reservoir with an agent level sensor and continually receiving agent level measurements at a processor from the agent level sensor. A dispense rate is then calculated with a processor based on the agent level measurements received over time, and the remaining agent time is calculated based on a current agent level measurement and the dispense rate.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Applicants have recognized that a problem with existing vaporizer systems is that the anesthesia level indication of remaining anesthetic agent in the vaporizer reservoir is difficult to interpret and provides clinicians with insufficient information in order to determine when the anesthetic agent remaining in the vaporizer reservoir will be used up. Specifically, currently available agent level indicators, such as sight glasses, do not provide clinicians with sufficient in formation to easily determine how much anesthetic delivery time remains based on the current level of anesthetic agent in the vaporizer reservoir. Since usage rates of various agents are different, and concentration settings will vary between patients, it can be difficult for a clinician to gage remaining agent time based merely on the agent level indication, such as through a sight glass. Thus, for example, it can be difficult for a clinician to determine whether the remaining agent in the vaporizer reservoir will be sufficient to provide anesthesia for a remaining portion of an ongoing procedure, or whether the clinician should order a refill of one or more anesthetic agents being delivered to the patient. Moreover, many healthcare facilities have tightened restrictions on anesthetic agents, requiring rigorous monitoring of anesthetic agent. Thus, a clinician may not be able to secure immediate delivery of anesthetic agent refill and may need to provide significant advanced notice prior to running out of agent in a vaporizer reservoir.

In view of the foregoing problems and challenges relating to management of anesthetic for vaporizer systems, the inventors developed the presently disclosed system and method of tracking anesthetic agent in a vaporizer reservoir wherein a dispense rate is calculated based on measurements within the vaporizer system and a remaining agent time is calculated based on a current agent amount and the dispense rate. In various embodiments disclosed herein, the dispense rate calculation may be based on measurements taken at one or more various locations within the vaporizer system, such as based on an agent level sensed at the vaporizer reservoir, based on measurements at the accumulator-injector that injects the anesthetic agent into the vaporizer chamber, and/or at the output of the vaporizer system. In various embodiments, dispense rate and remaining agent time may be redundantly calculated based on measurements at two or more locations in the vaporizer system, in order to provide a robust method and system for tracking anesthetic agent.

Figures 1, 2:
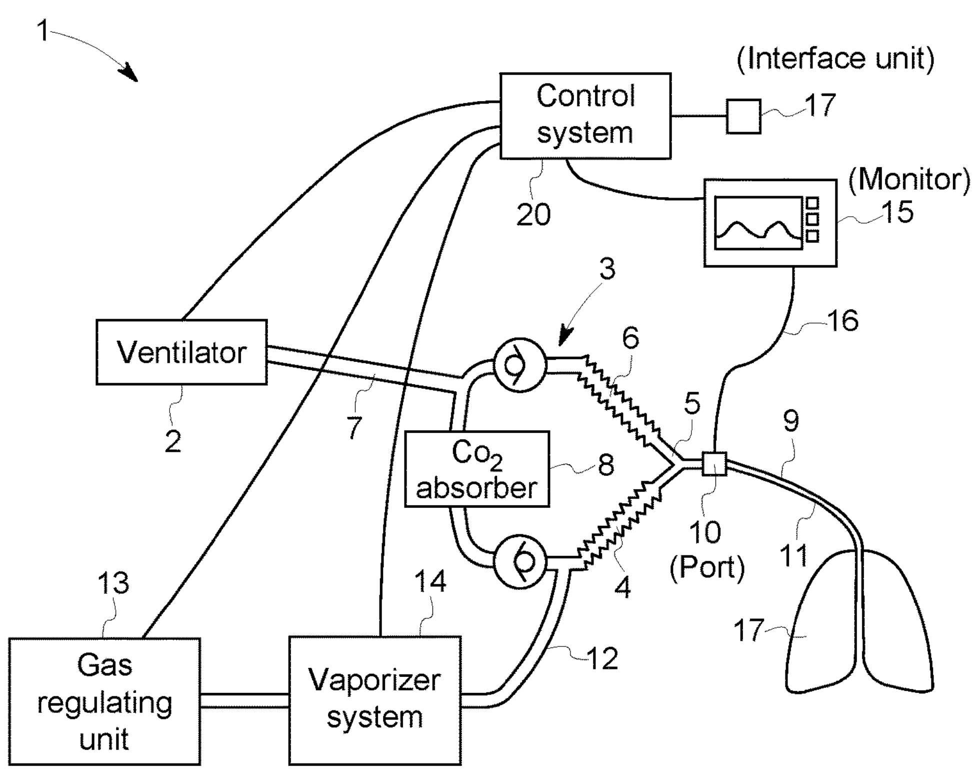
FIG. 1 schematically depicts an exemplary anesthesia system implementing the anesthesia agent tracking system and method of the present disclosure.
FIG. 2 schematically depicts an exemplary vaporizer system having an exemplary anesthetic agent tracking system for tracking anesthetic in a vaporizer reservoir.

FIG. 1 exemplifies the disclosed system and method for tracking anesthetic agent, which is utilized within an anesthesia environment and in connection with a vaporizer system. Ventilator 2 fills patient lungs during inspiration by pressurizing the breathing circuit 3. Breathing circuit comprises of inspiration limb 4, Y-piece 5, expiration limb 6, ventilator limb 7, CO2 absorber 8, and patient limb 9. Inspiration and expiration limbs include unidirectional valve to direct the inspiration and expiration gas flow to respective limbs. Patient limb includes gas monitor sampling port 10 and intubation tube 11 connecting the patient with the breathing circuit. In operation, ventilator receives the expired gas from the patient during expiration and stores the gas for the next inspiration. At inspiration the gas is guided through CO2 absorber, where the CO2 is removed, to inspiration limb and further to patient lungs. Breathing gas is brought into the breathing circuit from fresh gas line 12. The breathing gas is a mixture of O2, N2O or N2 (air) from gas regulating unit 13 and volatile agents vaporized into this gas stream in the vaporizer 14. Alternatively patient may be breathing spontaneously. In spontaneous breathing the ventilator comprises reservoir collecting the exhalation gas and therefrom patient breathing action receives inspiration gas.

Monitor device 15, i.e. gas monitor, may be of a sidestream type drawing a sample gas stream from the sampling port 10 through sampling line 16 for analysis with the sensors within the monitor. Alternatively the monitor device may be of mainstream type where the gas analysis sensors are located directly at the patient limb instead of the sampling port. Monitor device 15 is further electrically connected to control system 20, which is further connected to the actuators (gas regulating unit 13, and/or vaporizer 14) closing the control loop. This controller compares the measured values with the set target, which may be user-set targets or software-controlled targets, and tunes the actuators to match the measured values with the setting. For example, the user can set the target by using an interface unit 17. In certain embodiments, the concentration setting 56 may be controlled by a setting of the dial 26, such as provided at the top of the vaporizer reservoir 25 (FIG. 2). In other embodiments, the concentration setting 56 may be inputted by a clinician, such as via an interface unit 17 for the anesthesia system 1 or directly for the vaporizer system 14.

FIG. 2 depicts one embodiment of a vaporizer system 14 of the anesthesia system 1, which includes one embodiment of an anesthetic agent tracking system 18 according to the present disclosure. The vaporizer system 14 includes a vaporizer reservoir 25 that houses liquid anesthetic agent to be dispensed for inhalation by the patient, such as into the breathing circuit 3 for the patient. The vaporizer reservoir 25 is filled by inserting additional anesthetic agent through the fill port 27, such as by pouring anesthetic agent from a refill bottle into the vaporizer reservoir 25. A pump 31 is connected to the vaporizer reservoir 25 to pump liquid through the supply line 33 to the accumulator 35. Liquid anesthetic agent is accumulated at the accumulator to a particular pressure. The liquid anesthetic agent in the accumulator 35 is heated by heater 36 to a set temperature. The heated and pressurized liquid anesthetic agent is then injected into a gas flow in the vaporizer chamber 44. Specifically, the liquid anesthetic agent is provided through an injector 41 into the vaporizer chamber 44, where it becomes anesthetic vapor and mixes with the fresh gas supplied to the vaporizer chamber 44 from the gas regulating unit 13. Dispensing of the anesthetic agent through the injector 41 is controlled by opening and closing of the valve 38 to provide a specified amount of anesthetic agent in order to meet a concentration setting 56. Namely, depending on the amount of fresh gas being supplied by the gas regulating unit 13, the valve 38 is controlled to dispense a specified amount of anesthetic agent into the fresh gas stream in order to reach a concentration setting 56, such as an anesthesia concentration setting set by a clinician. As will be understood by a person having ordinary skill in the art in light of the present disclosure, the period and frequency of the valve 38 opening can be controlled, in consideration of the pressure and temperature of the anesthetic agent, in order to deliver a precise amount of anesthetic agent into the gas stream in the vaporizer chamber 44. As will also be understood by a person having ordinary skill in the art in light of the present disclosure, certain embodiments may employ other dispensing means for dispensing the anesthetic agent into the gas stream for delivery to the patient. Several such dispensing means are known in the art, such as an accumulator/dispenser comprising a diaphragm separating a liquid anesthetic volume from a gas volume.

The anesthetic agent tracking system 18 includes various sensors configured to assist in determining a dispense rate of anesthetic agent. The sensors provide information to a computing system 200 (FIG. 3) containing an agent time module 22 configured to calculate remaining agent time based on the provided information. In various embodiments, the computing system 200 may be incorporated in a control system housed locally in the vaporizer system 14, or may be incorporated in the control system 20 for the anesthesia system 1. In still other embodiments, the vaporizer system 14 may be incorporated within other patient care systems or devices, such as a critical care ventilator or a bypass machine. In such embodiments, the computing system 200 housing the agent time module 22 may be housed locally within the vaporizer system 14, or may be provided within the control system of a relevant host device.

In the example of FIG. 2, sensors are provided to measure information regarding or relating to the amount of anesthesia that is being dispensed to the patient, such as to determine a dispense rate and/or a dispensed agent amount, and that information can then be used to calculate remaining agent time. A gas temperature sensor 48 is configured to measure a temperature 59 of the mixed gas provided from the vaporizer chamber 25. A gas pressure sensor 49 is configured to measure pressure 60 of the mixed gas provided from the vaporizer chamber 44. A gas concentration sensor 50 is configured to measure the anesthetic concentration 62 in the mixed gas provided from the vaporizer chamber 44, which is the anesthetic concentration of the gas outputted from the vaporizer system 14, such as through the gas line 12 (FIG. 1). In other embodiments, the gas concentration sensor 50 may be eliminated, and the remaining agent time 70 may instead be calculated based on a concentration setting 56 for controlling delivery of anesthetic agent in the mixed gas provided from the vaporizer chamber 44. A gas mass flow sensor 43 is also provided, and configured to measure a gas flow rate 58 entering or exiting the vaporizer chamber 44. In the depicted embodiment, the gas mass flow sensor 43 is provided between the gas regulating unit 13 and the vaporizer chamber 44, and thus is configured to measure the gas flow rate 58 of the fresh gas entering the vaporizer chamber 44. In other embodiments, the gas mass flow sensor 43 may be provided to measure the gas flow rate 58 of gas that has exited the vaporizer chamber 44, such as providing the gas mass flow sensor 43 at or near the gas concentration sensor 50. Accordingly, the remaining agent time 70 is calculated based on the gas flow rate 58, the mixed gas pressure 60, the mixed gas temperature 59, and the anesthetic concentration (which may be the anesthetic agent concentration 62 measured by the gas concentration sensor 50, or may be a concentration setting 56 or liquid agent mass flow measurement between the accumulator and the injector 41). In one embodiment, a sensor pack may be provided at the output of the vaporizer chamber 44, such as along the gas line 12 between the vaporizer system 14 and the breathing circuit 3, providing the gas temperature sensor 48, the gas pressure sensor 49, the gas concentration sensor 50, and the gas mass flow sensor 43.

In various embodiments, other or additional remaining agent time calculations may be performed, such as secondary and or tertiary remaining agent time calculations determined based on measurements taken at other locations within the vaporizer system 14. For example, the dispense rate and remaining agent time (e.g., 70, 72, or 73) can be determined based on information measured at the injector 41 and/or the accumulator 45. A temperature sensor 37 is provided at the accumulator 35 (or alternatively at any location providing a sufficiently accurate measurement of temperature of the liquid anesthetic agent provided to the injector 41), which provides an injector temperature 64 measurement of the temperature of liquid anesthetic agent provided to the injector 41. A pressure sensor 39 is configured to measure the pressure of anesthetic agent provided to the injector 41 through the valve 38. An injection frequency 66 is also provided, which is the rate and duration that the valve 38 is open to dispense anesthetic agent into the vaporizer chamber 44 from the injector 41. Based on that measured and supplied information, the agent time module 22 calculates the remaining agent time. In the depicted embodiment, remaining agent time calculations based on information gathered at and around the injector 41 is provided as a secondary remaining agent time 72, which can be used as a validation check on the primary remaining agent time 70 calculation and as backup in the event of a failure of systems related to the primary calculation. However, in other embodiments, the remaining agent time calculation based on the above-described measurements at the accumulator 35 and the injector 41 may be used as a primary remaining agent time 70 calculation.

Alternatively or additionally, the dispense rate and remaining agent time (e.g., 70, 72, or 73) can be determined based on information measured at the vaporizer reservoir 25. For example, the dispense rate may be calculated as a trend determination based on agent level measurements 68 by one or more agent level sensors 28, 29. The remaining agent time may then be calculated accordingly. For example, the vaporizer reservoir measurements may be provided and utilized by the anesthetic agent tracking system 18 to generate the tertiary remaining agent time 73, which may be utilized as a validation check on the primary remaining agent time 70 calculation and as backup in the event of a failure of systems related to the primary and secondary calculation.

In various embodiments, the agent level sensors 28, 29 may be any of various types of sensors capable of determining the level of liquid anesthetic agent in the vaporizer reservoir 25. For example, the agent level sensor 28 may be a time-of-flight infrared or ambient light sensor. To provide just one example, the agent level sensor 28 may be a proximity and ambient light sensing module, such as the VL 6180X sensor by STMicroelectronics N. V. In the depicted example, a pressure sensor 29 senses a pressure exerted by the anesthetic agent at the bottom of the vaporizer reservoir 25. Thus, based on the known properties of the liquid anesthetic agent, the agent level can be determined based on the pressure measured by the pressure sensor 29. Alternatively, the agent level sensor may be an infrared sensor or an ultrasonic sensor, such as positioned on a top side of the interior of the vaporizer reservoir 25 and able to measure a level of the anesthetic agent liquid. The pressure sensor 29 may be, for example, a differential pressure transducer (DP) measuring a high pressure at the bottom of the vaporizer reservoir 25 and a low pressure at a top of the vaporizer reservoir 25. Thereby, the pressure sensor 29 can measure a difference between the gas pressure at the top of the vaporizer reservoir 25 and the combined gas and liquid level pressure at the bottom of the vaporizer reservoir 25. Thereby, the liquid pressure can be isolated, which can provide a liquid level measurement. When determining the liquid level based on the liquid pressure measurement, specific gravity is preferably taken into account. The agent level may be provided by the following equation, where pressure is the hydrostatic head pressure measured at the bottom of the vaporizer reservoir 25 (cm water column, psi, bar, etc.) and the specific gravity is the specific gravity of the specific liquid anesthetic agent contained in the vaporizer reservoir 25:

$$\text{Agent Level} = \frac{\text{Pressure}}{\text{Specific Gravity}}$$

$$\text{Specific Gravity} = \frac{\text{Density of Agent}}{\text{Density of Water}}$$

The resulting agent level is then provided as a height of the liquid being measured, such as in centimeters or millimeters.

Various vaporizer systems 14 may implement one, two, or all three of the methods described above for calculating remaining agent time. In certain embodiments, certain remaining agent time calculations may be prioritized over others. For example, the remaining agent time calculation based on measurements at the output of the vaporizer system 14 may be prioritized as the primary remaining agent time 70 calculation. One or more of the other calculation methods may then be provided as secondary remaining agent time 72 and tertiary remaining agent time 73. For example, the remaining agent time calculation based on measurements at the injector 41 and/or the accumulator 35 may be outputted as a secondary remaining agent time 72, and remaining agent time calculated based on measurements at the vaporizer reservoir 25 may be outputted as a tertiary remaining agent time 73. In other embodiments, different priorities may be assigned to the various remaining agent time calculations.

The remaining agent time 70, 72, 73 calculations may be compared to one another and/or compared to a threshold in order to assess consistency of the calculations and/or identify when one of the calculations is inaccurate, such as due to a faulty sensor. For example, the remaining agent time 70, 72, 73 values may be compared to determine whether they are within an acceptable range of one another. If one of the values is considered an outlier, the anesthetic agent tracking system 18 may be configured to conduct a diagnostic to assess the inputs, such as the sensors and sensor values, to identify any potential problem therewith. If, for example, a problem is identified with a primary remaining agent time 70 value, then the secondary remaining agent time 72 and/or the tertiary remaining agent time 73 may be utilized in its place. For example, if a fault is detected within the system, or the primary remaining agent time 70 value is determined to be inaccurate, then the secondary remaining agent time 72 and/or the tertiary remaining agent time 73 may be displayed to the clinician and utilized for purposes of alarming when the remaining agent time is sufficiently low. For example, one or more of the remaining agent time values 70, 72, 73 may be compared to one or more threshold time values for purposes of alerting a clinician to the time status. A threshold time value may be preset, such that when the remaining agent time 70, 72, 73 reaches the threshold an agent time expiring alert 72 is generated. In certain embodiments, the threshold time value may be set by a clinician, such as at the beginning of a case, to account for the type of case and agent being used.

In other embodiments, the system 18 may automatically determine the threshold time value, such as based on the type of agent being used, and/or the history of the concentration setting 56 throughout the case. For instance, where certain agents are likely to take longer to obtain or to be inputted into the vaporizer reservoir 25, the threshold time value may be set relatively higher. Likewise, where a trend in the concentration setting 56 and/or the measured anesthetic concentration 62 indicates that the anesthetic concentration may be increased in the future, the threshold time value may be relatively higher to account for the possibility of the anesthetic concentration being increased in the near future and thus the dispense rate increasing. Similarly, where the trend of the concentration setting 56 and/or the measured anesthetic concentration 62 is decreasing, such as indicating the conclusion of a surgical procedure, the threshold time value may be slightly lowered to account for the likelihood that the anesthetic concentration is likely to be decreased in the near future, which will lower the dispense rate and the amount of time that the current anesthetic amount will last.

Figure 4:
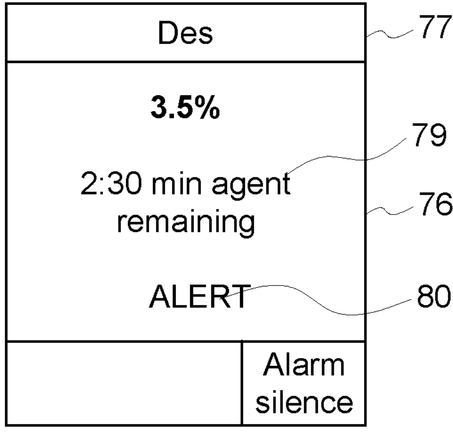
FIG. 4 depicts an exemplary display screen displaying remaining agent time.

FIG. 4 depicts one embodiment of a display screen 76 providing a time remaining indicator 79 indicating the remaining agent time 70, 72, 73. In the depicted example, the display screen 76 is also providing a visual alert 80, such as resulting from an agent time expiring alert 75 generated because the remaining agent time 70, 72, 73 is below the threshold time value. The display screen 76 also provides an agent identifier 77 indicating that the relevant anesthetic agent is expiring. A concentration value of 3.5% is also indicated, which may be based on the concentration setting 56. An alarm silence input is also exemplified, such as for a clinician to silence an agent time expiring alert 75.

Figure 5:
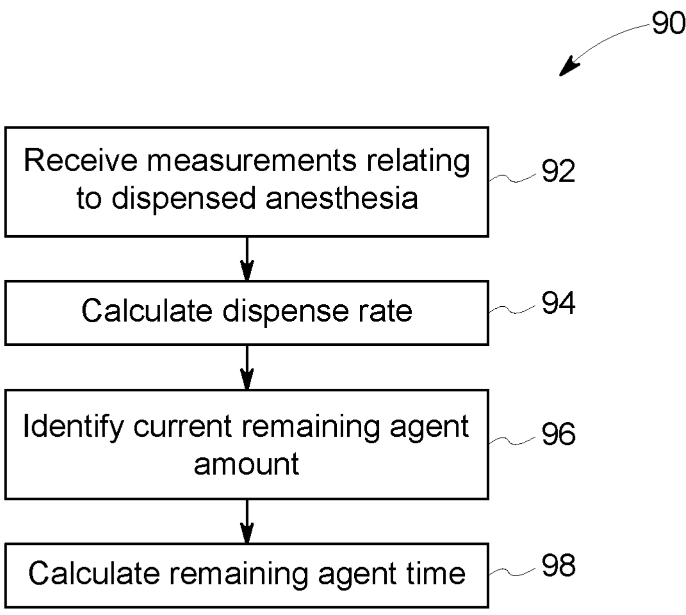
FIGS. 5-10 provide flow charts exemplifying methods, or portions thereof, of tracking anesthetic agent in a vaporizer reservoir.

FIGS. 5-10 depict various embodiments of methods 90, or portions thereof, for tracking anesthetic agent in a vaporizer reservoir 25. In FIG. 5, measurement's relating to dispensed anesthesia are received as step 92, such as those exemplified in FIG. 2. A dispense rate is calculated at step 94 based on the measured values and/or other inputs, such as according to the examples provided herein. A current remaining agent amount is identified at step 96 and the remaining agent time is calculated at step 98, such as dividing the current remaining agent amount by the dispense rate.

Figure 6:
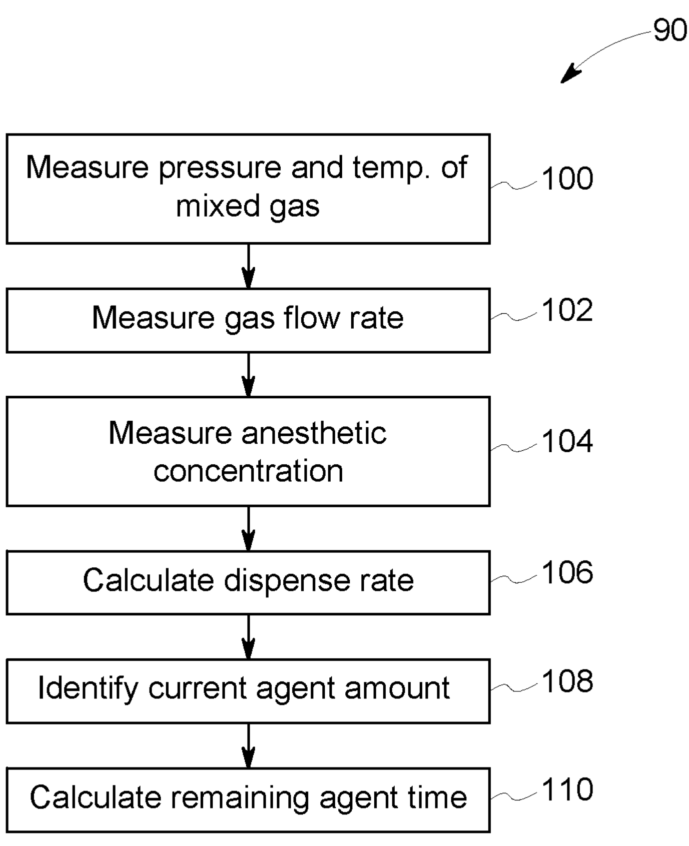

FIG. 6 depicts one embodiment of calculating remaining agent time based on measurements at the output of the vaporizer system 14. Pressure and temperature of a mixed gas exiting the vaporizer chamber 44 are measured at step 100, such as by the gas pressure sensor 49 and temperature sensor 48. A gas flow rate entering or exiting the vaporizer chamber 44 is measured at step 102. For example, the gas flow rate may be measured by a gas mass flow sensor 43 positioned between the gas regulating unit 13 and the vaporizer chamber 44, as is exemplified in the system depicted in FIG. 2. Alternatively, the flow rate of the mixed gas may be measured after the output of the vaporizer chamber 44, in which case the mass of the agent in the gas will need to be subtracted out from the gas flow rate value utilized to calculate the remaining agent time. The anesthetic concentration is measured at step 104, measuring the concentration of the relevant anesthetic agent in the mixed gas exiting the vaporizer chamber 44. In other embodiments, instead of measuring the anesthetic concentration, a concentration setting 56 may be utilized in its place, which may be assumed to provide an estimate of the anesthetic concentration in the output of the vaporizer chamber 44. The dispense rate is then calculated at step 106 based on the pressure and temperature of the mixed gas, the gas flow rate, and the anesthetic concentration. A current agent amount is identified at step 108. For example, the current agent amount may be a current agent level 68, such as the most recent output of one or more agent level sensors 28, 29. Alternatively, the current agent amount may be a calculated value based on an initial agent amount as is described and exemplified in FIG. 7. Remaining agent time is calculated at step 110 based on the dispense rate and the current agent amount.

Figure 7:
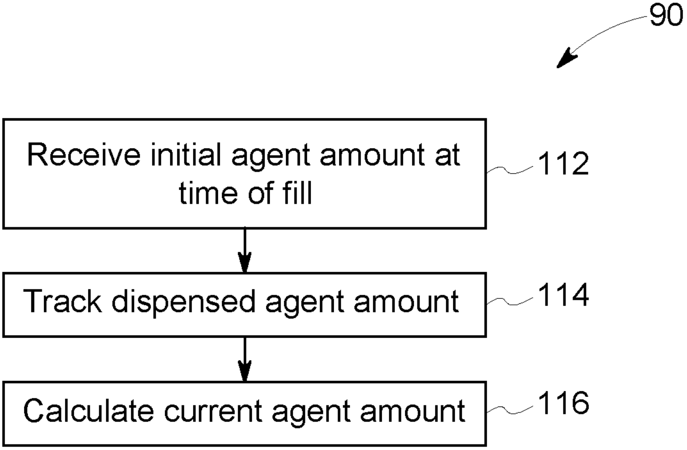

FIG. 7 depicts a method 90 portion for determining a current agent amount. An initial agent amount is received at step 112. For example, the initial agent amount may be an agent amount added to the vaporizer reservoir at the time of fill, thus providing a starting point fill level. The dispensed agent amount is tracked at step 114, such as by adding the calculated dispense rate values over time. Thus, a current agent amount can be determined by subtracting the dispensed amount from the initial agent amount. Such a method could be utilized where a sensed agent level value is not available, such as in the event of sensor failure or in a system where an agent level sensor is not provided. Where an agent level sensor is provided, current agent amount is determined based on the sensed agent level, such as by accounting for a known volume and/or geometry of the vaporizer reservoir to determine a volume of anesthetic agent based on the measured fill level. For example, user interface 17 for the system 1, or a dedicated user interface for the vaporizer system 14 may provide an input (such as a GUI button or a physical push button) that can be selected when a new bottle of agent has been added. In certain embodiments, one or more inputs may be selectable to signify a fixed amount of added agent. Alternatively, the user interface may provide the ability to input an added volume of agent.

Figure 8:
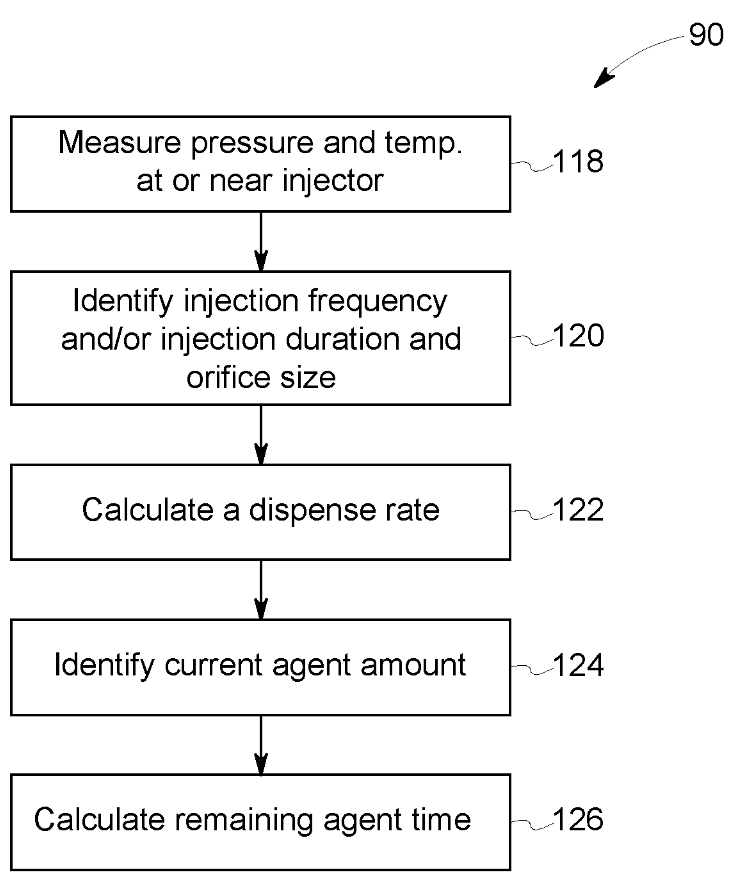

FIG. 8 depicts another embodiment of the remaining agent time calculation, which is based on measurements conducted at or near the injector. Specifically, a temperature and pressure are measured at or near the injector at step 118, such as by the temperature sensor 37 and the pressure sensor 39 exemplified in the schematic representation at FIG. 2. Factors are identified at step 120 relating to an injection rate of the injector 41, which include an orifice size of the injector outlet, such as an injector outlet diameter, and injection frequency and/or injection duration. The injection frequency is the cycle frequency of the valve 38 in the injector 41 per unit time. The injection duration of the injector 41 is the duration per unit time that the valve 38 is open, and thus permitting injection of anesthetic agent into the vaporizer chamber 44.

A dispense rate is then calculated at step 122 based on the injection factors identified at step 120 and the temperature and pressure measured at step 118. For example, the dispense rate may be calculated based on a known agent density at the measured pressure and temperature, which may be provided in a look up table, to calculate a discharge coefficient. The discharge coefficient may be utilized in an orifice function that accounts for the injection parameters, including the injection frequency, injection duration, and orifice size, to calculate a dispensed volume per unit time from the injector. For example, the dispense rate may be provided in milliliters per second. A current agent amount is identified at step 124, such as based on an agent level measurement measured by an agent level sensor 28, 29 or a calculated agent amount as exemplified in FIG. 7. Remaining agent time is then calculated at step 126 based on the current agent amount and the dispense rate.

Figure 9:
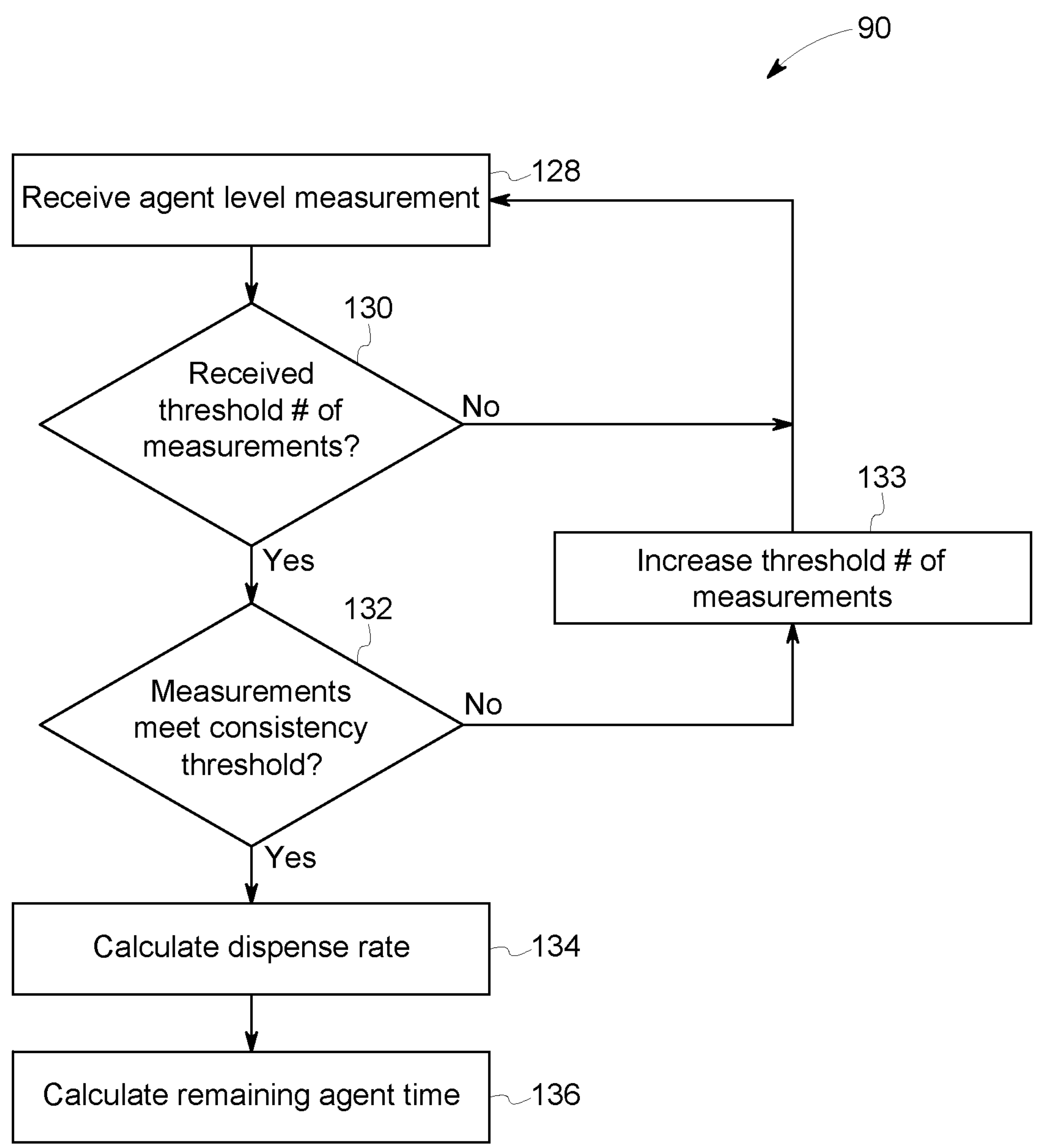

FIG. 9 depicts a method of calculating remaining agent time based on agent level measurements 68 from an agent level sensor 28, 29. Agent level measurements 68 are continually received at step 128 as they are measured by an agent level sensor 28, 29. As described above, in one embodiment, an agent level sensor may be a pressure sensor 29. In another embodiment, the agent level sensor may be a time-of-flight infrared sensor 28. In one exemplary embodiment, such as where a time-of-flight infrared sensor 28 is utilized, the agent level sensor may have a 10 Hz update rate, thus providing ten agent level measurements 68 per second. At step 130, the method determines whether a threshold number of measurements have been received. For example, the threshold may come into play upon start up of the vaporizer system 14, upon refill of the vaporizer reservoir 25, or upon a change in the concentration setting 56. Namely, at least a threshold number of measurements need to be accumulated in order to calculate remaining agent time.

For example, the threshold number of measurements may be set based on the geometry of the vaporizer reservoir 25, the type of agent contained in the vaporizer reservoir 25, or other parameters that would affect the dispense rate, and thus the rate of change of the agent level measurement. For example, the geometry of the vaporizer reservoir, such as the height to volume or height to cross-sectional area ratio affects the rate at which the agent level changes per dispensed volume of anesthetic agent. For example, the agent level will change much quicker in a tall vaporizer reservoir with a small cross-sectional area than it will in a shorter vaporizer reservoir with a larger cross-sectional area. Thus, the sensitivity and accuracy of the respective sensors, and thus the number of samples required for an accurate trend analysis, has a greater affect in the flatter vaporizer reservoir than in the taller one. Thus, the threshold number of measurements may be higher for the flatter vaporizer reservoir than the taller one. Similarly, where the dispense rate is higher, the agent level in the vaporizer reservoir will change more quickly, which can decrease the required threshold number of agent level measurements for calculating a sufficiently accurate trend. Namely, certain agents require higher or lower concentration settings, and certain patients require higher or lower concentration settings. Where a concentration setting is relatively high, the threshold number of measurements required to determine a trend may be lower than scenarios where the concentration setting is relatively low and thus the change in agent level per unit time is less.

Step 132 determines whether the measurements meet a consistency threshold. For example, step 132 may examine the threshold number of most recent measurements. If the consistency threshold is not met, then the threshold number of measurements may be increased at step 133 to require acquisition of more data for calculation of the remaining agent time. For example, the consistency threshold may require that the measurements be within a predetermined value of one another and/or follow a consistent trend, such as requiring at least a subset of the agent level measurements to follow a consistent decreasing pattern. Once a set of agent level measurements meeting the consistency threshold is obtained, then a dispense rate is calculated at step 134 based on the trend exhibited by the agent level measurements. Various methods of trend analysis may be used to calculate, or predict, the rate of change of the agent level measurement, or the dispense rate, for the given concentration setting 56. The remaining agent time is then calculated at step 136 based on the dispense rate and the current agent level measurement. For example, a current agent level measurement may be calculated based on a filtered value derived from the agent level sensor data, such as to eliminate noise or remove erroneously high or low values.

Figure 10:
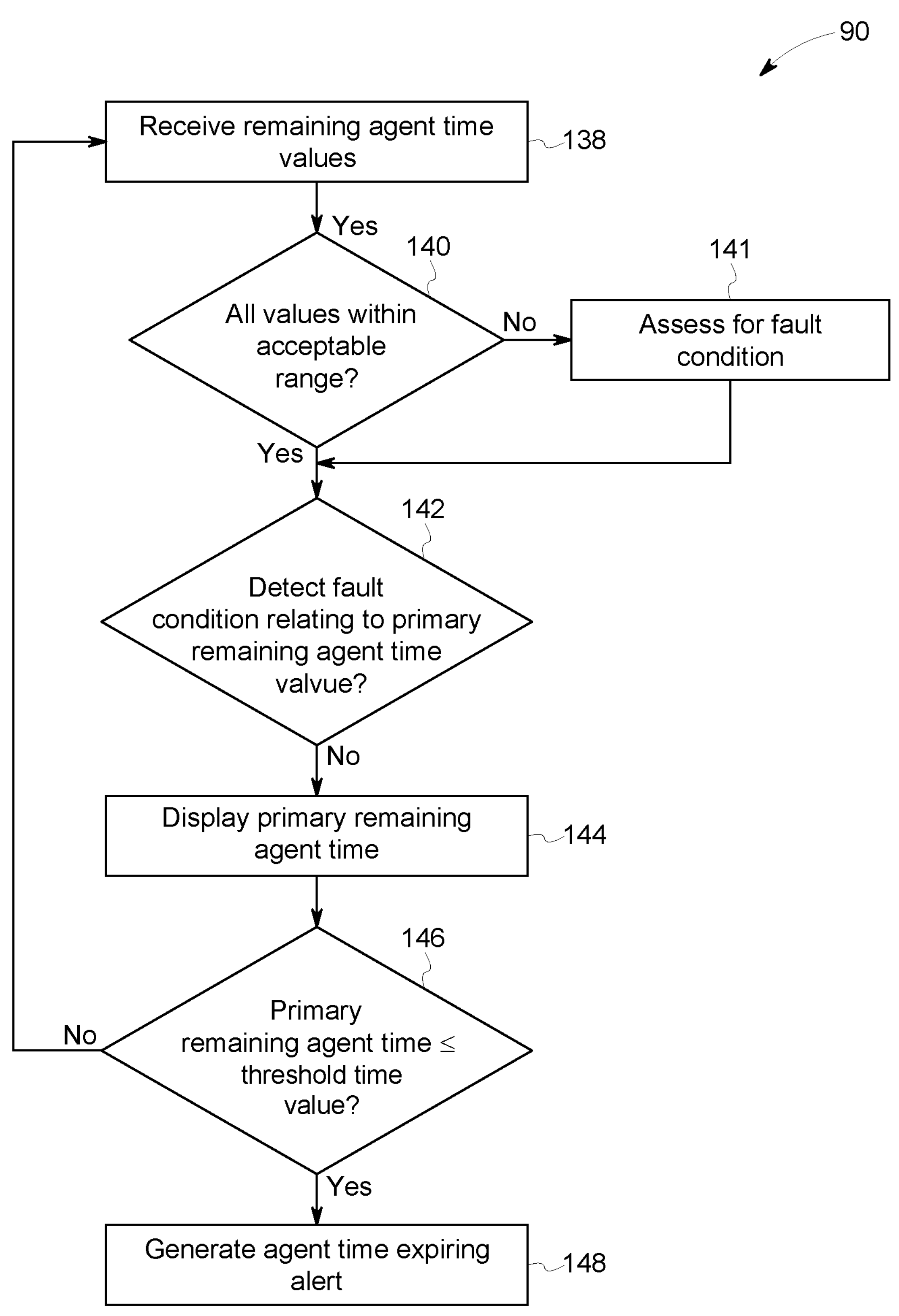

FIG. 10 depicts exemplary method steps for comparing two or more remaining agent time calculations, such as those generated by the exemplary methods depicted in FIGS. 6, 8, and 9. The remaining agent time calculations are received at step 138, such as remaining agent time calculations calculated based on data for comparable time periods in the agent dispensing process. The remaining agent time values are compared to one another at step 140 to determine whether they are within acceptable range of one another or whether there is an outlier value. If one of the values is not within an acceptable range, then the anesthetic agent tracking system 18 may assess at step 141 whether a fault condition can be detected, such as whether a faulty sensor is causing an inaccurate remaining agent time calculation.

Step 142 determines whether a fault condition is detected relating to the primary remaining agent time value. For example, one of the remaining agent time values may be assigned as a primary value and the others as back up values or secondary and tertiary values. Assuming that no fault is detected relating to the primary remaining agent time value, then the primary remaining agent time is displayed at step 144, such as on a display relating to the vaporizer system 14 or on the anesthesia system 1 or other host device.

The primary remaining agent time is then compared to a threshold time value at step 146 to assess whether an agent time expiring alert should be generated at step 148. In various embodiments, the agent time expiring alert may be an audio and/or visual alert generated by a user interface of the vaporizer system 14, or by audio or visual user interface devices (e.g., interface unit 17) incorporated in the anesthesia system 1 or other host device. In other embodiments, the display and threshold analysis may be conducted based on two or more of the remaining agent time values, such as an average of those remaining agent time values that are within the acceptable range as analyzed at step 140.

Figure 3:
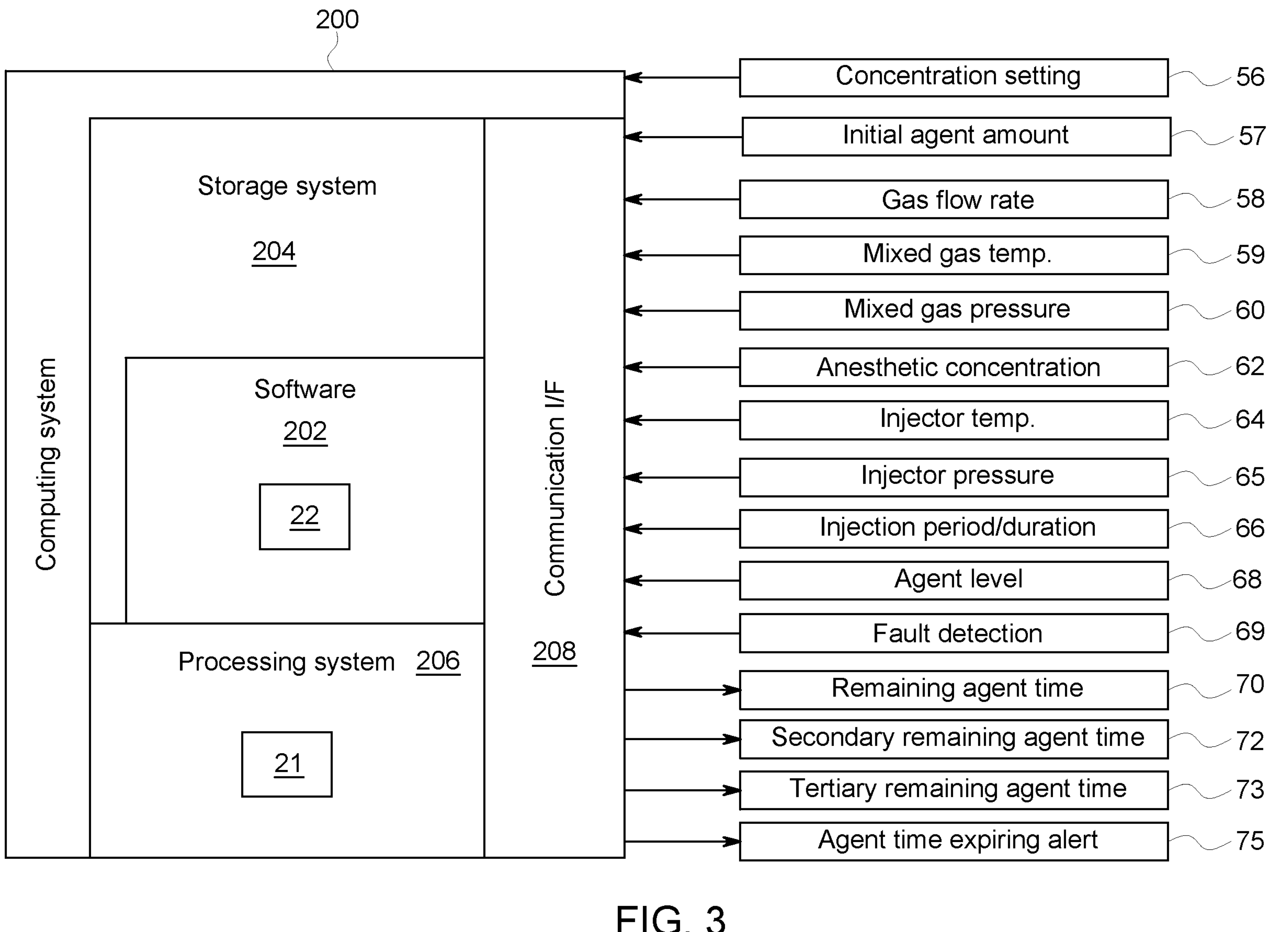
FIG. 3 schematically depicts an exemplary computing system having an agent time module executing one or more methods for tracking anesthetic agent.

FIG. 3 is a schematic diagram of a computing system 200 comprising part of the anesthetic agent tracking system 18 having an agent time module 22 that operates as described herein to calculate one or more remaining agent time values 70, 72, 73. The computing system 200 includes a processing system 206, storage system 204, software 202, and a communication interface 208. The processing system 206 loads and executes software 202 from the storage system 204, including the agent time module 22, which is an application within the software 202. The agent time module 22 include computer-readable instructions that, when executed by the computing system 200 (including the processing system 206), direct the processing system 206 to operate as described in herein in further detail, including to execute the steps to calculate remaining agent time 70, 72, 73.

Although the computing system 200 as depicted in FIG. 3 includes one software 202 encapsulating one agent time module 22, it should be understood that two or more software elements, or modules, may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes the processor 34, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204 can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as the various temperature, pressure, and agent level sensors described herein. The communication interface 208 may provide wired or wireless communication with such sensor devices and/or with a data aggregator or hub device that receives the measurement data from the various sensors and communicates it, such as via wireless communication means, to the computing system 200.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. An anesthetic agent tracking system for tracking anesthetic agent in a vaporizer reservoir within an anesthesia vaporizer system, the anesthetic agent tracking system comprising:

a mass flow sensor configured to measure a gas flow rate entering or exiting a vaporizer chamber;

a gas pressure sensor configured to measure a pressure of a mixed gas provided from the vaporizer chamber; and a processor to:

calculate a remaining agent time based on at least the gas flow rate, the pressure of the mixed gas, and an anesthetic concentration in the mixed gas;

configured to provide the remaining agent time for display to a clinician;

receive an initial agent amount;

track a dispensed agent amount based on the gas flow rate, the pressure of the mixed gas, a temperature of the mixed gas, and the anesthetic concentration in the mixed gas;

calculate a current agent amount based on the initial agent amount and the dispensed agent amount; and calculate the remaining agent time based further on the current agent amount.

2. The anesthetic agent tracking system of claim 1, further comprising a gas temperature sensor configured to measure the temperature of the mixed gas provided from the vaporizer chamber.

3. The anesthetic agent tracking system of claim 1, further comprising a vaporizer gas concentration sensor configured to measure the anesthetic concentration in the mixed gas provided from the vaporizer chamber.

4. The anesthetic agent tracking system of claim 1, wherein the anesthetic concentration is a concentration setting for controlling delivery of the anesthetic agent in the mixed gas provided from the vaporizer chamber.

5. The anesthetic agent tracking system of claim 1, further comprising:

an agent level sensor that senses an agent level of the anesthetic agent in the vaporizer reservoir; and wherein the processor is to:

determine the current agent amount based on the agent level;

calculate the remaining agent time based further on the current agent amount.

6. The anesthetic agent tracking system of claim 5, wherein the processor is to compare the remaining agent time to a threshold time value and generate an agent time expiring alert if the remaining agent time is less than the threshold time value.

7. The anesthetic agent tracking system of claim 5, further comprising:

an injector pressure sensor configured to sense a pressure of the anesthetic agent provided to an injector delivering a liquid anesthetic agent to the vaporizer chamber;

an injector temperature sensor configured to sense a temperature of the anesthetic agent provided to the injector; and wherein the processor is to calculate a secondary remaining agent time based on the current agent amount, the pressure of the anesthetic agent, the temperature of the anesthetic agent, an orifice size of the injector, and at least one of an injection frequency and an injection duration of the injector.

8. The anesthetic agent tracking system of claim 7, wherein the processor is to: receive a fault detection regarding at least one of the gas pressure sensor, a gas temperature sensor, or a vaporizer gas concentration sensor; and configured to provide the secondary remaining agent time for display to the clinician.

9. An anesthetic agent tracking system for tracking anesthetic agent in a vaporizer reservoir within an anesthesia vaporizer system, the system comprising: an injector pressure sensor configured to sense a pressure of the anesthetic agent provided to an injector delivering a liquid anesthetic agent to a vaporizer chamber;

an injector temperature sensor configured to sense a temperature of the anesthetic agent provided to the injector; and a processor to:

identify a current agent amount;

calculate a remaining agent time based on the pressure of the anesthetic agent, the temperature of the anesthetic agent, an orifice size of the injector, and at least one of an injection frequency or an injection duration of the injector; and configure to provide the remaining agent time for display to a clinician.

10. The anesthetic agent tracking system of claim 9, wherein the processor is to calculate the remaining agent time further based the current agent amount.

11. The anesthetic agent tracking system of claim 9, wherein the current agent amount is based on an agent level of anesthetic agent in the vaporizer reservoir sensed by an agent level sensor.

12. The anesthetic agent tracking system of claim 11, further comprising:

a mass flow sensor configured to measure a gas flow rate entering or exiting the vaporizer chamber;

a gas pressure sensor configured to sense a pressure of a mixed gas provided from the vaporizer chamber;

a gas temperature sensor configured to sense a temperature of the mixed gas provided from the vaporizer chamber;

a vaporizer gas concentration sensor configured to measure an anesthetic concentration in the mixed gas provided from the vaporizer chamber;

wherein the processor is to calculate a secondary remaining agent time based on the agent level, the gas flow rate, the pressure of the mixed gas, the temperature of the mixed gas, and the anesthetic concentration in the mixed gas.

13. The anesthetic agent tracking system of claim 11, wherein the processor is to compare the remaining agent time to a threshold time value and generate a low agent alert if the remaining agent time is less than the threshold time value.

14. A method for tracking anesthetic agent in a vaporizer reservoir within an anesthesia vaporizer system, the method comprising:

measuring a gas flow rate entering or exiting a vaporizer chamber;

measuring a pressure of a mixed gas provided from the vaporizer chamber;

identifying an anesthetic concentration in the mixed gas provided from the vaporizer chamber, wherein identifying the anesthetic concentration comprises measuring, with a vaporizer gas concentration sensor, the anesthetic concentration in the mixed gas provided from the vaporizer chamber, or receiving a concentration setting for controlling delivery of an anesthetic agent from the vaporizer chamber;

identifying a current agent amount of the anesthetic agent in the vaporizer reservoir;

calculating a dispense rate based on the anesthetic concentration, the gas flow rate, and the pressure of the mixed gas;

calculating a remaining agent time based on at least the current agent amount and the dispense rate;

providing the remaining agent time for display to a clinician;

measuring a pressure of the anesthetic agent provided to an injector delivering anesthetic agent to the vaporizer chamber;

measuring a temperature of the anesthetic agent provided to the injector; and calculating a secondary remaining agent time based on the current agent amount, the pressure of the anesthetic agent, the temperature of the anesthetic agent, an orifice size of the injector, and at least one of an injection frequency and an injection duration of the injector.

15. The method of claim 14, further comprising:

comparing at least one of the remaining agent time and the secondary remaining agent time to a threshold time value; and generating an agent time expiring alert if the at least one of the remaining agent time or the secondary remaining agent time is less than the threshold time value.

16. The method of claim 15, wherein identifying the agent amount comprises receiving an agent level from an agent level sensor in the vaporizer chamber.

17. The method of claim 15, further comprising:

receiving an initial agent amount;

tracking a dispensed agent amount based on the dispense rate over time;

wherein the agent amount is identified based on the initial agent amount and the dispensed agent amount; and calculating the remaining agent time based further on the agent level.

* * * * *